(12) United States Patent
Clarke et al.

(10) Patent No.: US 6,303,673 B1
(45) Date of Patent: Oct. 16, 2001

(54) PHOTOCHROMIC COMPOUNDS

(75) Inventors: David A. Clarke, Brighouse; Bernard Mark Heron, Yorkshire; Christopher David Gabbutt; John David Hepworth, both of Lancashire; Steven Michael Partington; Stephen Nigel Corns, both of Huddersfield, all of (GB)

(73) Assignee: James Robinson Limited, Huddersfield (GB)

( * ) Notice: Subject to any disclaimer, the term of this patent is extended or adjusted under 35 U.S.C. 154(b) by 0 days.

(21) Appl. No.: 09/529,704

(22) PCT Filed: Oct. 19, 1998

(86) PCT No.: PCT/GB98/03124

§ 371 Date: Jun. 19, 2000

§ 102(e) Date: Jun. 19, 2000

(87) PCT Pub. No.: WO99/20630

PCT Pub. Date: Apr. 29, 1999

(30) Foreign Application Priority Data

Oct. 20, 1997 (GB) .................................................. 9722127

(51) Int. Cl.[7] .......................... C07D 498/10; G03C 1/685
(52) U.S. Cl. .................................. 524/89; 544/71; 524/90
(58) Field of Search ..................... 544/101, 71; 524/110, 524/89.9

(56) References Cited

U.S. PATENT DOCUMENTS 5,559,231   9/1996   Yamamoto et al. ................... 544/70

FOREIGN PATENT DOCUMENTS

| 0449669 | 10/1991 | (EP) . |
|---|---|---|
| 600668 | 6/1994 | (EP) . |
| 9604590 | 2/1996 | (WO) . |
| 9611926 | 4/1996 | (WO) . |

OTHER PUBLICATIONS

Derwent Abstract of JP 62033184 (1987).
V. Yu. Nedoshivin, N.L. Zaichenko, A.I. Shienok and V.S. Marevtsev, Russ. Chem. Bull. vol. 44, No. 4, 1995, p. 712.
V. Yu. Nedoshivin, A.V. Lyubimov, N.L. Zaichenko, V.S. Marevtsev, and M. I. Cherkashin, Bull. Acad. Sci. USSR (Div. Chem. Sci.) Engl. Transl. 1989, vo. 39, p. 2363.
T. Ya. Vlasenko, A.V. Lyubimov, N.L. Zaichenko, V.S. Marevtsev and M.I. Cherkashin, Bull. Acad. Sci. USSR (Div. Chem. Sci) Engl. Transl. 1990, vol. 39, p. 1375.
G. Luchina, I. Yu. Sychev, V.S. Marevtsev, T. Ya. Vlasenko, Yu. O. Khamchukov, and M.I. Cherkashin, Bull. Russ, Acad. Sci. Engl. Transl. 1992, vol. 41, p. 2152.
Patent Abstracts of Japan, vol. 11, No. 214, Jul. 10, 1987.
Patent Abstracts of Japan, vol. 16, No. 369, Aug. 10, 1992.

*Primary Examiner*—Richard L. Raymond
(74) *Attorney, Agent, or Firm*—Stevens, Davis, Miller & Mosher, L.L.P.

(57) ABSTRACT

A photochromic compound has the formula (I) wherein $R^1$ is selected from the group including substituted amino aryl moieties, substituted cyclic amino aryl moieties and substituted N-indolinoaryl or N-tetrahydroquinolino aryl groups, $R^3$ is selected from the group including linear or branched $C_1$–$C_{20}$ alkyl, linear or branched $C_2$–$C_{20}$ alkenyl or polyalkenyl, $C_2$–$C_{20}$ alkynyl or polyalkynyl, aryl, heteroaryl, linear or branched $C_1$–$C_{20}$ alkyl aryl, linear or branched $C_1$–$C_{20}$ alkyl-cycloalkyl or -bicycloalkyl or -tricycloalkyl or substituted -cycloalkyl or -bicycloalkyl or -tricycloalkyl, linear or branched $C_1$–$C_{20}$ haloalkyl or perhaloalkyl, linear or branched $C_1$–$C_{20}$ alkoxyalkyl or peralkoxyalkyl, linear or branched $C_1$–$C_{20}$ alkylthioalkyl or peralkylthioalkyl, linear or branched $C_1$–$C_{20}$ amino alkyl or peraminoalkyl, $C_3$–$C_{20}$ cycloalkyl or substituted cycloalkyl, $C_4$–$C_{20}$ bicycloalkyl or substituted bicycloalkyl, $C_6$–$C_{20}$ tricycloalkyl or substituted tricycloalkl or linear or branched $C_1$–$C_{20}$ hydroxyalkyl or perhydroxyalkyl; $R^4$ and $R^5$ which may be the same or different are $R^3$ or $R^4$ and $R^5$ are conjoined to form a spiro linked $C_3$–$C_{20}$ cyclic system or substituted cyclic system; and wherein $R^2$ and $R^6$ are each selected from $R^3$ or hydrogen, halogen, nitro, nitroso, amino, acetamido, $C_2$–$C_{10}$ N-alkylamido, alkoxycarbonyl, nitrile, carboxy, hydroxy, aryloxy, $C_1$–$C_{10}$ alkoxy, a heteroatom which is O or N or S or P which in turn can be bonded either singly or multiply to carbon, oxygen, sulphur or nitrogen, $C_1$–$C_5$ alkoxy or alkylthio or aryl or aryloxy or multiples thereof.

23 Claims, No Drawings

PHOTOCHROMIC COMPOUNDS

The present invention relates to novel hyperchromic, rapid responding, photochromic spiroindolinonaphthoxazines which are of green or green-blue colouring, and to articles and compositions containing them.

Photochromism is a well established phenomenon and has been detailed in "Photochromism: Molecules and Systems," Studies in Organic Chemistry, vol. 40, eds. H. Dürr and H. Bouas-Laurent, Elsevier, 1990. Much effort has been directed to exploring the photochromic properties of naphth[2,1-b][1,4]oxazines and many derivatives of this ring system are known. However, there are few examples of photochromic compounds based on the naphth[1,2-b][1,4]oxazine system to date, see for example Jpn. Kokai Tokkyo Koho JP 62 33,184 (1997 Chem. Abstr. 107, 187531) and Eur. Patent EP 0 449 669 A1 [1991]. These patents disclose compounds which possess the basic structural unit illustrated below and which show blue-purple photochromism upon irradiation:

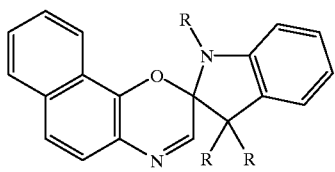

1,3-dihydrospiro[2H-indole-2,2'-[2H]naphth[1,2-b][1,4]oxazine]

We have now devised a novel modification of the naphth[1,2-b][1,4]oxazine system which permits access to green or blue-green colouring photochromic dyes with excellent colourability, rapid photochromic response, high fatigue resistance and a favourable background colour. Moreover, by judicious choice of substituents greatly differing rates of bleaching can be achieved.

In one aspect, the invention provides a photochromic compound having the general formula (I):

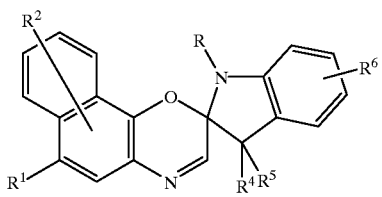

wherein:

(a) —$R^1$ is selected from the following aminoaryl moieties:

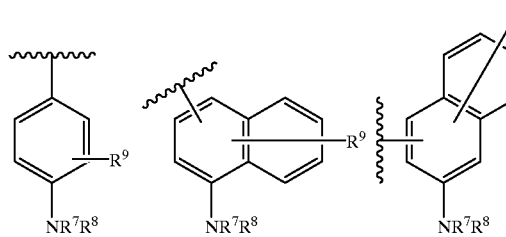

in which $R^7$ and $R^8$, which may be the same or different, are each selected from a linear or branched $C_1$–$C_{20}$ alkyl group, an aryl group, a heteroaryl group, a linear or branched $C_1$–$C_{20}$ alkylaryl group, a linear or branched $C_1$–$C_{20}$ alkyl -cycloalkyl or -bicycloalkyl or -tricycloalkyl or substituted -cycloalkyl or -bicycloalkyl or -tricycloalkyl group, a linear or branched $C_1$–$C_{20}$ haloalkyl or perhaloalkyl group, a linear or branched $C_1$–$C_{20}$ alkoxyalkyl or peralkoxyalkyl group, a linear or branched $C_1$–$C_{20}$ alkylthioalkyl or peralkylthioalkyl group, a linear or branched $C_1$–$C_{20}$ aminoalkyl or peraminoalkyl group, a $C_3$–$C_{20}$ cycloalkyl or substituted cycloalkyl group, a $C_4$–$C_{20}$ bicycloalkyl or substituted bicycloalkyl group, a $C_6$–$C_{20}$ tricycloalkyl or substituted tricycloalkyl group, a linear or branched $C_1$–$C_{20}$ hydroxyalkyl or a perhydroxyalkyl group; or (b) —$R^1$ is selected from cyclic aminoaryl moieties in which $R^7$ and $R^8$ are conjoined according to the following structures:

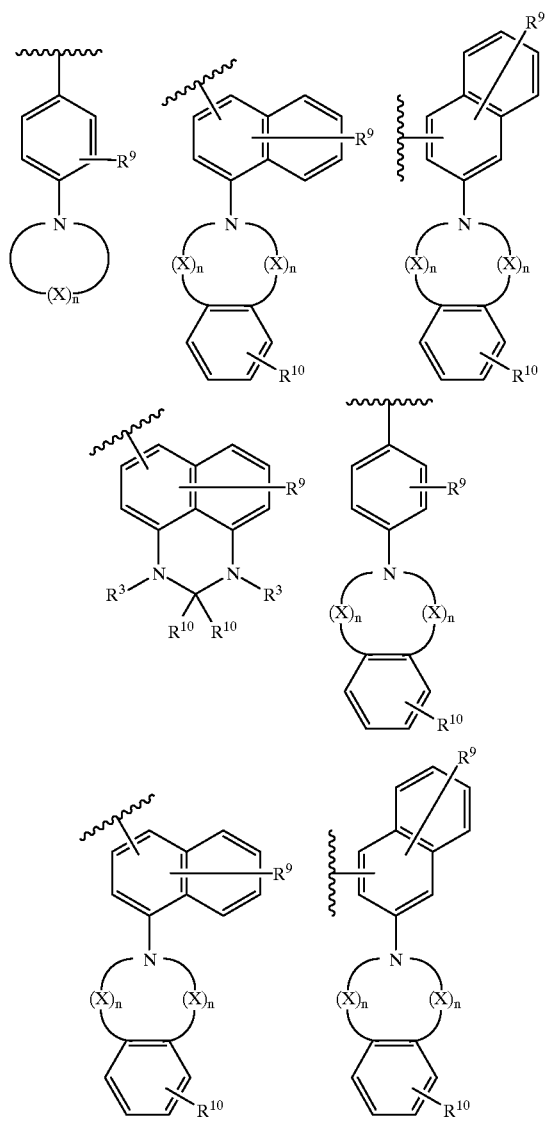

-continued

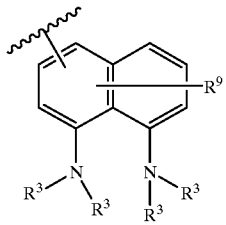

wherein the size of the nitrogen containing ring is from 3 to 40 atoms (inclusive of the N atom) and may incorporate one or more of the same or different groups of atoms (X) which may be arranged in any sequence and where X may be selected from $CH_2$, $CHR^7$, $CR^7R^8$, CHaryl, $C(aryl)_2$, C(alkyl,aryl), O, S, S(O), $S(O)_2$, NH, N-alkyl, N-aryl, P-alkyl, P-aryl, P(O)alkyl P(O)aryl, P(O)Oalkyl; wherein $R^7$ and $R^8$ may each be selected from those substituents specified above; or (c) —$R^1$ may represent an N-indolinoaryl or N-tetrahydroquinolino aryl substituent of the structure:

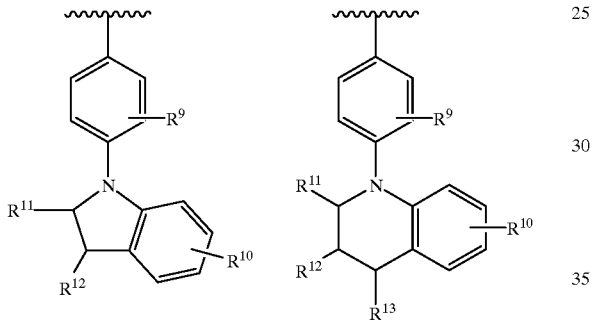

wherein $R^{11}$, $R^{12}$ and $R^{13}$ are each a $C_1$–$C_5$ linear or branched alkyl group or aryl group, or any two groups selected from $R^{11}$, $R^{12}$ and $R^{13}$ may be conjoined to form a ring of 5 to 8 atoms (including those of the indoline or tetrahydroquinoline ring); or (d) —$R^1$ may be represented by the structure (II) below, in which the N-atom is incorporated at the bridgehead position in a tricyclic nitrogen heterocycle, and p and q are both integers between 2 and 6 and may be the same or different;

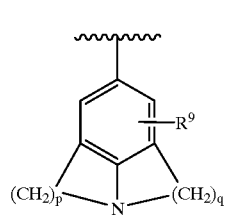

(II)

and wherein —$R^3$ is a linear or branched $C_1$–$C_{20}$ alkyl group, a linear or branched $C_2$–$C_{20}$ alkenyl or polyalkenyl group in any E or Z geometrical isomeric form, a $C_2$–$C_{20}$ alkyl or polyalkynyl group, an aryl group, a heteroaryl group, a linear or branched $C_1$–$C_{20}$ alkyl aryl group, a linear or branched $C_1$–$C_{20}$ alkyl -cycloalkyl or -bicycloalkyl or -tricycloalkyl or substituted -cycloalkyl or -bicycloalkyl or -tricycloalkyl group, of which the following are non-limiting illustrative examples:

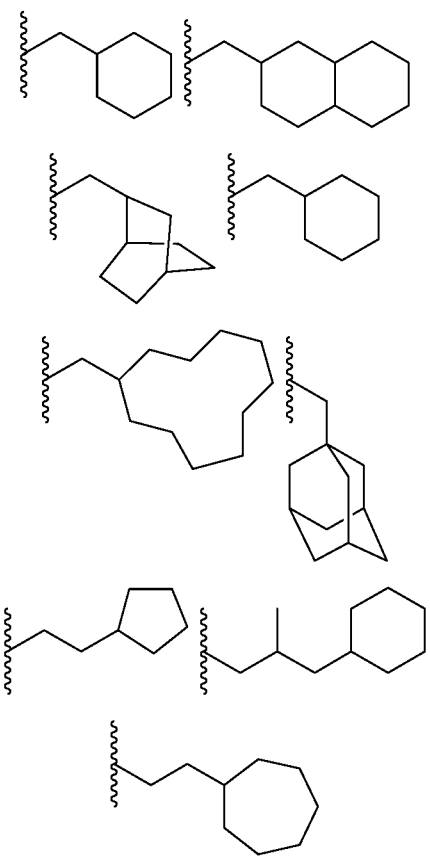

a linear or branched $C_1$–$C_{20}$ haloalkyl or perhaloalkyl group, a linear or branched $C_1$–$C_{20}$ alkoxyalkyl or peralkoxyalkyl group, a linear or branched $C_1$–$C_{20}$ alkylthioalkyl or peralkylthioalkyl group, a linear or branched $C_1$–$C_{20}$ aminoalkyl or peraminoalkyl group, a $C_3$–$C_{20}$ cycloalkyl or substituted cycloalkyl group, of which the following are non-limiting illustrative examples:

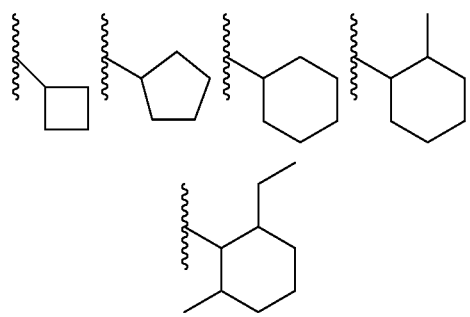

a $C_4$–$C_{20}$ bicycloalkyl or substituted bicycloalkyl group, of which the following are non-limiting illustrative examples:

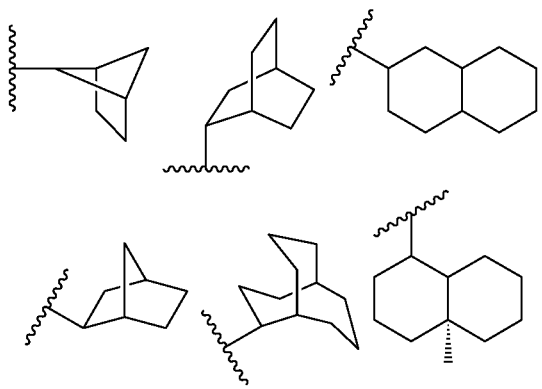

a $C_6$–$C_{20}$ tricycloalkyl or substituted tricycloalkyl group, such as for example:

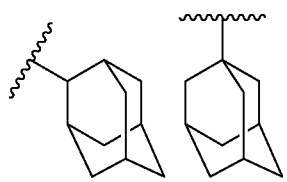

or a linear or branched $C_1$–$C_{20}$ hydroxyalkyl or perhydroxyalkyl group; and wherein —$R^4$ and —$R^5$, which may be the same or different, are each selected from the substituents specified for —$R^3$ above, or —$R^4$ and —$R^5$ may be conjoined to form a spiro linked $C_3$–$C_{20}$ cyclic system or substituted cyclic system; and wherein —$R^6$ of which there may be none, one or more than one, and which may be the same or different are each selected from H, $C_1$–$C_{20}$ linear or branched alkyl $C_1$–$C_{20}$ linear or branched alkoxy, $C_1$–$C_{20}$ linear or branched alkylthio, hydroxy, amino, $C_1$–$C_{20}$ linear or branched alkylamino, $C_1$–$C_{20}$ linear or branched dialkylamino, $C_1$–$C_{20}$ linear or branched alkyl arylamino, diarylamino, arylamino, benxylamino, dibenzylamino, $C_2$–$C_{20}$ linear or branched alkanoylamino, aroylamino and cyclic amino and wherein —$R^2$, $R^9$ and $R^{10}$ of which there may be none, one or more than one, and which may be the same or different, are each selected from hydrogen, halogen, nitro, nitroso, amino, acetamido, C2–C10 N-alkylamido, alkoxycarbonyl, nitrile, carboxy, hydroxy, aryloxy, C1–C10 alkoxy, a heteroatom which is O or N or S or P which in turn can be bonded either singly or multiply to carbon, oxygen, sulfur or nitrogen, C1–C5 alkoxy or allylthio or aryl or aryloxy or to multiples thereof, non-limiting illustrative examples of which are:

P(O)(OEt)$_2$, SO$_3$H, SO$_3$Et, SO$_2$H, SO$_2$Ph, SOMe, P(Ph)$_2$, P(O)(Ph)$_2$, N=N-aryl or —$R^2$, $R^9$ and $R^{10}$ may each be selected from those substituents specified for —$R^3$.

The invention also provides a process for making a photochromic compound of the invention, which process includes the following step:

wherein $R^1$, $R^3$, $R^4$ and $R^5$ are as defined in claim 1, or represent groups which can be replaced by, or modified to form, groups as defined respectively in claim 1, and wherein in the above step the reactants and/or product may also include substituents $R^2$ and $R^6$ as defined in claim 1, or such substituents are introduced subsequently. This is an expeditious and practicable synthesis of these materials.

The synthesis of naphthoquinone 2-oximes involves oximation of the readily available 4-aminoaryl-1,2-naphthoquinones, themselves accessible from 1,2-naphthoquinone or its 4-sulfonic acid salt. The methylene indoline derivative is readily available to those skilled in the art and the synthesis of these materials has been reviewed (see B. Robinson, "The Fischer Indole Synthesis," Wiley, Chichester, 1982). Formation of the naphthoxazine is accomplished by heating the reactants in a solvent such as, for example, an alcohol, aromatic hydrocarbon or an ether.

The photochromic properties exhibited by the novel spironaphthoxazines of the present invention, namely those of a desirable rate of bleaching of the coloured form at ambient temperatures, a high induced optical density of the coloured form and control of the shade of green or blue-green colour, coupled with their excellent fatigue resistance, render these compounds particularly useful as photochromic materials for incorporation into polymeric host materials such as optical elements, for example, so as to impart photochromic properties to the host materials. Examples of applications of the polymeric host materials containing photochromic materials of the present invention include lenses for sunglasses and ophthalmic lenses, optical filters and windows for. vehicles such as cars (including sunroofs), aircraft and ships and architectural and agricultural uses e.g. windows for, photochromic 'stained glass' windows and greenhouses, and toys, watches and their straps and novelty items. Additional uses may include incorporation into paints, inks and other like formulations. Other uses include device applications, such as electronic switches, non-linear optical devices and optical data storage.

The photochromic spironaphthoxazines of the present invention may be incorporated into the 'plastic' host material by well established protocols, for example as described in European Patent No. 0254020 or U.S. Pat. No. 5,066,818.

The high induced optical density of the photochromic compounds of the present invention enables the amount of the photochromic material required to impart a useful degree of photochromism to a polymeric host material or to a solution, to be greatly reduced, thereby enabling a considerable saving of synthetic effort and cost. Furthermore, the use of reduced quantities of the photochromic materials of th e present invention has the bonus that there is a consequent reduction in any undesirable colour that the photochromic materials may impart in the bleached state, either by way of inherent colour of the material itself or by the formation of coloured fatigue/degradation products through use of the photochromic material.

Typical host materials are optically clear polymer materials, such as polymers of polyol (allyl carbonate)-monomers, polyacrylates such as polymethylmethacrylates, cellulose acetate, cellulose triacetate, cellulose acetate propionate, cellulose acetate butyrate, poly(vinyl acetate), poly(vinyl alcohol), polyurethanes, polycarbonate, polyethylene terephthalate, polystyrene, poly(triethyleneglycol dimethacrylate), poly(diethyleneglycol-bis(allyl carbonate)) and various copolymer mixes.

Among the preferred compounds of the invention are a 1,3-dihydro-1-isobutyl-3,3-dimethyl-6'-(4-N,N-diethylaminophenyl)-spiro[2H-indole-2,2'[2H[naphth[1,2-b][1,4]oxazine], 1,3-dihydro-3,3-dimethyl-1-neopentyl-6'-(4-N,N-diethylaminophenyl)-spiro[2H-indole-2,2'[2H] naphth[1,2-b][1,4]oxazine], 5-acetamido-1,3-dihydro-1,3,3-trimethyl-6'-(4-N,N-diethylaminophenyl)-spiro[2H-indole-2,2'[2H]naphth[1,2-b][1,4]oxazine],1,3-dihydro-1-isobutyl-3,3,4,7-tetramethyl-6'-(4-N,N-diethylaminophenyl)-spiro [2H-indole-2,2'[2H]naphth[1,2-b][1,4]oxazine],1,3-dihydro-1,3,3-trimethyl-6'-(4-N,N-diethylaminophenyl)-spiro[2H-indole-2,2'[2H]naphth[1,2-b][1,4]oxazine],4-(4-N,N-diethylaminophenyl)-1,2-naphthoquinone-2-oxime, 4-(4-N,N-dimethylaminophenyl-1,2,-naphthoquinone-2-oxime, 4-(4-pyrrolidinophenyl)-1,2-naphthoquinone-2-oxime.

In order that the invention may be more fully understood, the following examples are given by way of illustration only.

EXAMPLE 1

(a) 4-(4-N,N-Diethylaminophenyl)-1,2-naphthoquinone

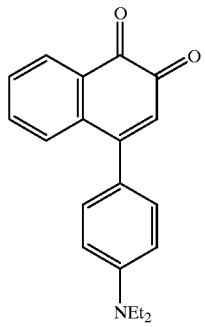

A solution of N,N-diethylaniline (0.05 mol) in methanol (20 cm³) was added dropwise over 10 mins to a stirred suspension of 1,2-naphthoquinone4-sulfonic acid sodium salt (0.05 mol) in methanol (20% aqueous) (350 cm³) at room temperature. On completion of the addition, the mixture was allowed to stir for 24 hrs whereupon the dark blue solid that had precipitated was collected by vacuum filtration, washed well with water and allowed to air dry. Yield=42%, m.p.=165–195° C.

(b) 4-(4N,N-Diethylaminophenyl)-1,2-naphthoquinone-2oxime

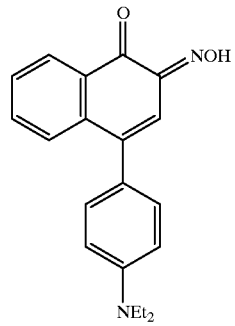

A solution of hydroxylamine hydrochloride (0.08 mol) in anhydrous ethanol (50 cm³) was added dropwise to a stirred solution of 4-(4-N,N-diethylaminophenyl)-1,2-naphthoquinone (0.02 mol) in warm anhydrous ethanol (250 cm³). The mixture was refluxed until thin layer chromatography indicated that no 4-(4-N,N-diethylaminophenyl)-1,2-naphthoquinone remained. The mixture was cooled in ice, diluted with water and the brown precipitate was collected by vacuum filtration and washed with water and air dried. Yield=75%, m.p.=176–178° C. The homogeneity of this material was verified by tlc and nmr and its structure was confirmed by X-ray crystallography.

(c) 1,3-Dihydro-1-isobutyl-3,3-dimethyl-6'-(4-N,N-diethylaminophenyl)-spiro-[2H-indole-2,2'[2H] naphth[1,2-b][1,4]oxazine]

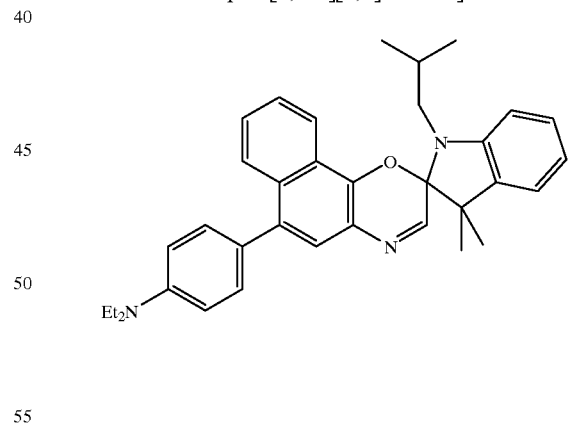

A solution of 4-(4-N,N-diethylaminophenyl)-1,2-naphthoquinone2-oxime (0.005 mol) and 1-isobutyl-3,3-dimethyl-2-methyleneindoline (0.005 mol) in anhydrous ethanol (70 cm³) was refluxed until examination of the reaction mixture by thin layer chromatography indicated that none of the 4-(4-N,N-diethylaminophenyl)-1,2-naphthoquinone-2-oxime remained. The mixture was cooled, reduced in volume and the precipitated product collected by vacuum filtration washed with a little cold ethanol and dried. Yield=66%, m.p.=166.5–168.5° C., $\lambda_{max}$= 614 nm in PhMe upon irradiation.

EXAMPLE 2

(a) 4-(4-N,N-Dimethylaminophenyl)-1,2-naphthoquinone

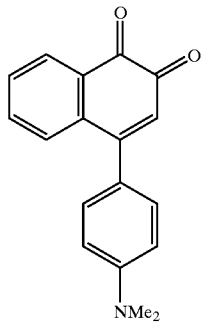

A solution of N,N-dimethylaniline (0.05 mol) in methanol (20 cm³) was added dropwise over 10 mins to a stirred suspension of 1,2-naphthoquinone-4-sulfonic acid sodium salt (0.05 mol) in methanol (20% aqueous) (350 cm³) at room temperature. On completion of the addition, the mixture was allowed to stir for 24 hrs whereupon the dark blue solid that had precipitated was collected by vacuum filtration, washed well with water and allowed to air dry. Yield=43%, m.p.=182–186° C.

(b) 4-(4-N,N-Dimethylaminophenyl)-1,2-naphthoquinone-2-oxime

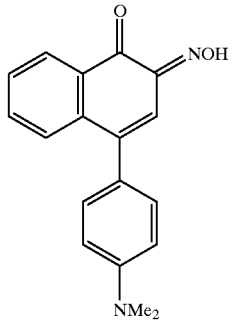

A solution of hydroxylamine hydrochloride (0.08 mol) in anhydrous ethanol (50 cm³) was added dropwise to a stirred solution of 4-(4-N,N-dimethylaminophenyl)-1,2-naphthoquinone (0.02 mol) in warm anhydrous ethanol (250 cm³). The mixture was refluxed until thin layer chromatography indicated that no 4-(4-N,N-dimethylaminophenyl)-1,2-naphthoquinone remained. The mixture was cooled in ice, diluted with water and the red brown precipitate was collected by vacuum filtration and washed with water and air dried. Yield=60%, m.p.=201–207° C.

(c) 1,3-Dihydro-3,3-dimethyl-1-neopentyl-6'-(4-N,N-dimethylaminophenyl)-spiro[2H-indole-2,2'[2H]naphth[1,2-b][1,4]oxazine]

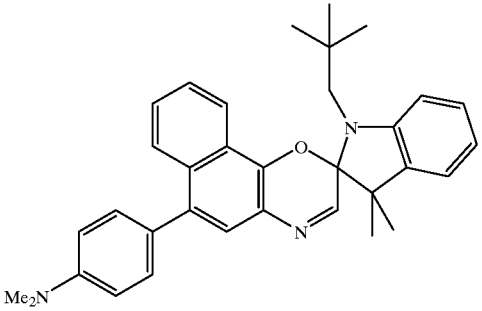

A solution of 4-(4-N,N-dimethylaminophenyl)-1,2-naphthoquinone-2-oxime (0.005 mol) and 3,3-dimethyl-1-neopentyl-2-methyleneindoline (0.005 mol) in anhydrous ethanol (70 cm³) was refluxed until examination of the reaction mixture by thin layer chromatography indicated that none of the 4-(4-N,N-dimethylaminophenyl)-1,2-naphthoquinone-2-oxime remained. The mixture was cooled, reduced in volume and the precipitated product collected by vacuum filtration washed with a little cold ethanol and dried. Yield=69%, m.p.=189.5–192.0° C., $\lambda_{max}$=625 nm in PhMe upon irradiation.

EXAMPLE 3

(a) 4-(4-Pyrrolidinophenyl)-1,2-naphthoquinone

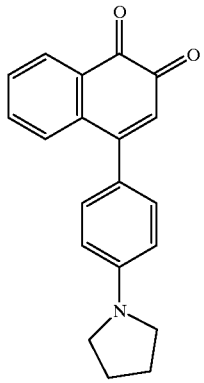

A solution of N-phenylpyrrolidine (0.05 mol) in methanol (20 cm³) was added dropwise over 10 mins to a stirred suspension of 1,2-naphthoquinone-4-sulfonic add sodium salt (0.05 mol) in methanol (20% aqueous) (350 cm³) at room temperature. On completion of the addition, the mixture was allowed to stir for 24 hrs whereupon the dark blue solid that had precipitated was collected by vacuum filtration, washed well with water and allowed to air dry. Yield=50%, m.p.=244–265° C. (decomp.).

(b) 4-(4-Pyrrolidinophenyl)-1,2-naphthoquinone-2-oxime

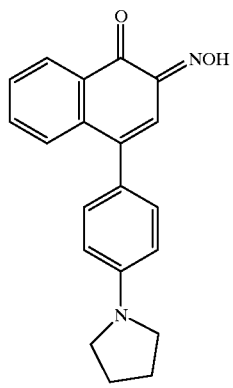

A solution of hydroxylamine hydrochloride (0.08 mol) in anhydrous ethanol (50 cm³) was added dropwise to a stirred solution of 4-(4-pyrrolidinophenyl)-1,2-naphthoquinone (0.02 mol) in warm anhydrous ethanol (250 cm³). The mixture was refluxed until thin layer chromatography indicated that no 4-(4-pyrrolidinophenyl)-1,2-naphthoquinone remained. The mixture was cooled in ice, diluted with water and the brown precipitate was collected by vacuum filtration and washed with water and air dried. Yield=84%, m.p.= 278–300° C. (decomp.).

(c) 1,3-Dihydro-1-isobutyl-3,3-dimethyl-6'-(4-pyrrolidinophenyl)spiro[2H-indole-2,2'[2H]naphth[1,2-b][1,4]oxazine]

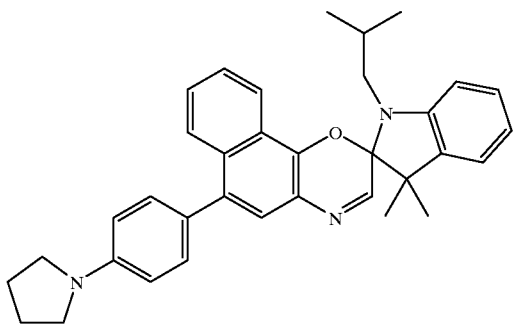

A solution of 4-(4-pyrrolidinophenyl)-1,2-naphthoquinone-2-oxime (0.005 mol) and 1-isobutyl-3,3-dimethyl-2-methyleneindoline (0.005 mol) in anhydrous ethanol (70 cm³) was refluxed until examination of the reaction mixture by thin layer chromatography indicated that none of the 4-(4-pyrrolidinophenyl)-1,2-naphthoquinone-2-oxime remained. The mixture was cooled, reduced in volume and the precipitated product collected by vacuum filtration washed with a little cold ethanol and dried. Yield= 19%, m.p.=242–245° C., $\lambda_{max}$=614 nm in PhMe upon irradiation.

Making use of the previously described general procedures above, the following compounds were obtained:

EXAMPLE 4

1,3-Dihydro1-isobutyl-3,3,4,7-tetramethyl-6'-(4-N,N-diethylaminophenyl)-spiro[2H-indole-2,2'[2H]naphth[1,2-b][1,4]oxazine]

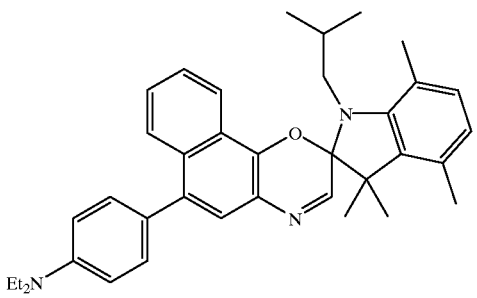

From 4-(4-N,N-dimethyl-aminophenyl)-1,2-naphthoquinone-2-oxime and 1-isobutyl-3,3,4,7-tetramethyl-2-methyleneindoline. Yield=51%, m.p.= 146.5–149.5° C., $\lambda_{max}$=622 nm in PhMe upon irradiation.

EXAMPLE 5

1,3-Dihydro-5-methoxy1,3,3-trimethyl-6'-(4-N,N-diethylaminophenyl)-spiro[2H-indole-2,2'[2H]naphth[1,2-b][1,4]oxazine]

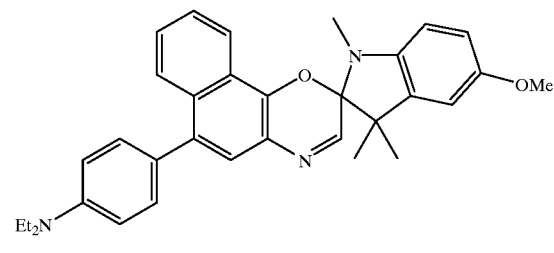

From 4-(4-N,N-diethylaminophenyl)-1,2-naphthoquinone-2-oxime and 5-methoxy-1,3,3 trimethyl-2-methyleneindoline. Yield=67%, m.p.=202–203° C., $\lambda_{max}$= 644 nm in PhMe upon irradiation.

EXAMPLE 6

5-Acetamido-1,3-dihydro-1,3,3-trimethyl-6'-(4-N,N-diethylaminophenyl)-spiro[2H-indole-2,2'[2H]naphth[1,2-b][1,4]oxazine]

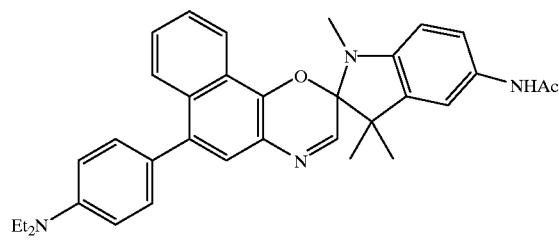

From 4-(4-N,N-diethylaminophenyl)-1,2-naphthoquinone-2-oxime and 5-acetamido-1,3,3-trimethyl-2-methyleneindoline. Yield=70%, m.p.=254.5–256.0° C., $\lambda_{max}$=622 nm in PhMe upon irradiation.

EXAMPLE 7

1,3-Dihydro-1-isobutyl-5,7-dimethoxy-3,3-dimethyl-6'-(4-N,N-diethylaminophenyl)spiro[2H-indole-2,2'[2H]naphth[1,2-b][1,4]oxazine]

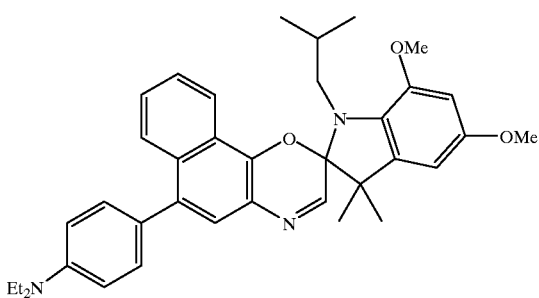

From 4-(4-N,N-diethylaminophenyl)-1,2-naphthoquinone-2-oxime and 5,7-dimethoxy-3,3-dimethyl-1-isobutyl-2-methyleneindoline. Yield=48%, m.p.=155–156° C., $\lambda_{max}$=638 nm in PhMe upon irradiation.

EXAMPLE 8

1,3-Dihydro-3,3-dimethyl-1-neopentyl-6'-(4-N,N-diethylaminophenyl)-spiro[2H-indole-2,2'[2H]naphth[1,2-b][1,4]oxazine]

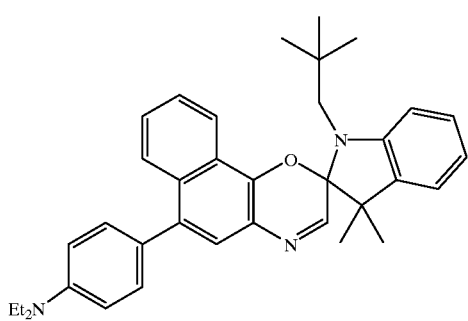

From 4-(4-N,N-diethylaminophenyl)-1,2-naphthoquinone-2-oxime and 3,3-dimethyl-1-neopentyl-2-methyleneindoline. Yield=57%, m.p.=188–191° C., $\lambda_{max}$=624 nm in PhMe upon irradiation.

Comparative Example 1

1,3-Dihydro-1,3,3-trimethyl-5-nitro-6'-(4-pyrrolidinophenyl)spiro-[2H-indole-2,2'[2H]naphth[1,2-b][1,4]oxazine]

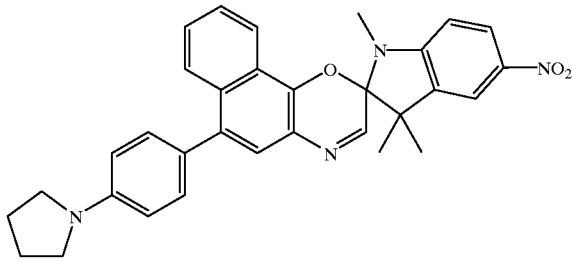

From 4-(4-pyrrolidinophenyl)-1,2-naphthoquinone-2-oxime and 1,3,3-trimethyl-2-methylene-5-nitroindoline. Yield=8%, m.p.=259.5–261.5° C., $\lambda_{max}$=592 and 470 (sh.) nm in PhMe upon irradiation.

Comparative Example 2

5-Cyano-1,3-dihydro-1,3,3-trimethyl-6'-(4-N,N-diethylaminophenyl)-spiro[2H-indole-2,2'[2H[naphth[1,2-b][1,4]oxazine]

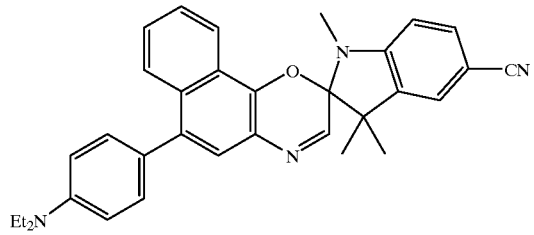

From 4-(4-N,N-diethylaminophenyl)-1,2-naphthoquinone-2-oxime and 5-cyano-1,3,3-trimethyl-2-methyleneindoline. Yield=10%, m.p.=245.5–247.0° C., $\lambda_{max}$=604 and 466 (sh.) nm in PhMe upon irradiation.

Comparative Example 3

1,3-Dihydro-1-isobutyl-3,3-dimethyl-5-trifluoromethyl-6'-(4-N,N-diethylaminophenyl)spiro[2H-indole-2,2'[2H]naphth[1,2-b][1,4]oxazine]

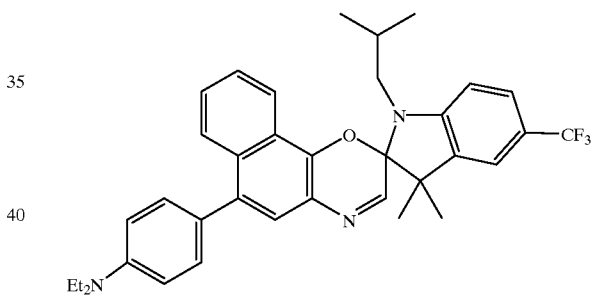

From 4-(4-N,N-diethylaminophenyl)-1,2-naphthoquinone-2-oxime and 3,3-dimethyl-1-isobutyl-2-methylene-5-trifluoromethylindoline. Yield=16%, m.p.=161.0–162.5° C., $\lambda_{max}$=604 nm in PhMe upon irradiation.

What is claimed is:

1. A photochromic compound having the general formula (I):

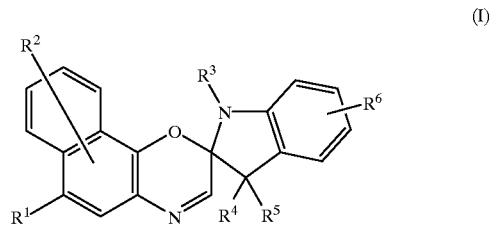

wherein:

(a) —$R^1$ is selected from the following aminoaryl moieties:

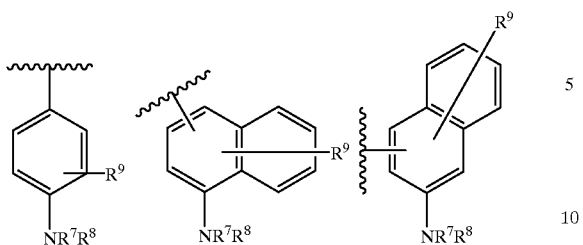

in which $R^7$ and $R^8$, which may be the same or different, are each selected from a linear or branched $C_1$–$C_{20}$ alkyl group, an aryl group, a heteroaryl group, a linear or branched $C_1$–$C_{20}$ alkylaryl group, a linear or branched $C_1$–$C_{20}$ alkyl -cycloalkyl or -bicycloalkyl or -tricycloalkyl or substituted -cycloalkyl or -bicycloalkyl or tricycloalkyl group, a linear or branched $C_1$–$C_{20}$ haloalkyl or perhaloalkyl group, a linear or branched $C_1$–$C_{20}$ alkoxyalkyl or peralkoxyalkyl group, a linear or branched $C_1$–$C_{20}$ alkylthioalkyl or peralkylthioalkyl group, a linear or branched $C_1$–$C_{20}$ aminoalkyl or peraminoalkyl group, a $C_3$–$C_{20}$ cycloalkyl or substituted cycloalkyl group, a $C_4$–$C_{20}$ bicycloalkyl or substituted bicycloalkyl group, a $C_6$–$C_{20}$ tricycloalkyl or substituted tricycloalkyl group, a linear or branched $C_1$–$C_{20}$ hydroxyalkyl or a perhydroxyalkyl group; or (b) —$R^1$ is selected from cyclic aminoaryl moieties in which $R^7$ and $R^8$ are conjoined according to the following structures:

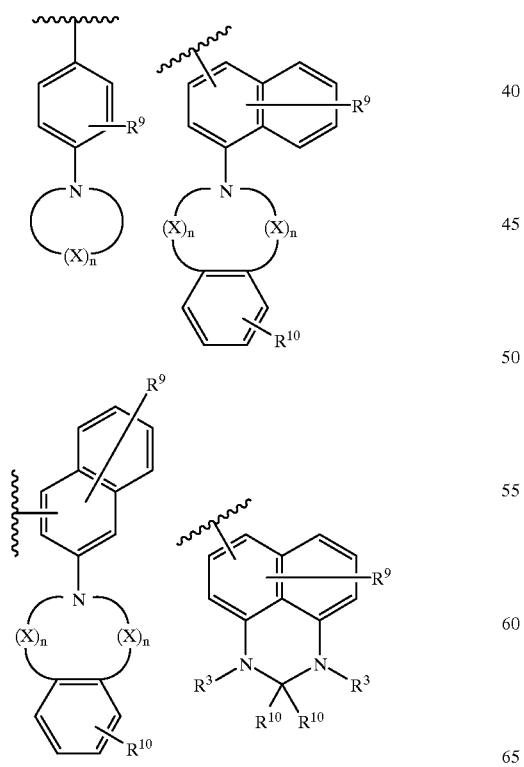

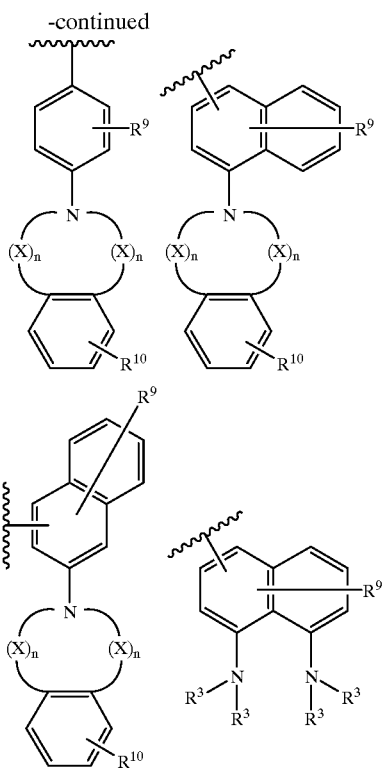

wherein the size of the nitrogen containing ring is from 3 to 40 atoms (inclusive of the N atom) and may incorporate one or more of the same or different groups of atoms (X) which may be arranged in any sequence and where X may be selected from $CH_2$, $CHR^7$, $CRR^7R^8$, CHaryl, $C(aryl)_2$, C(alkyl,aryl),O, S, S(O), $S(O)_2$, NH, N-alkyl, N-aryl, P-alkyl, P-aryl, P(O)alkyl, P(O)aryl, P(O)Oalkyl; wherein $R^7$ and $R^8$ may each be selected from those substituents specified above; or (c) —$R^1$ represents an N-indolinoaryl or N-tetrahydroquinolino aryl substituent of the structure:

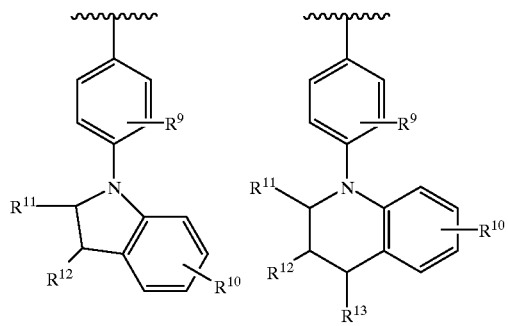

wherein $R^{11}$, $R^{12}$ and $R^{13}$ are each a $C_1$–$C_5$, linear or branched alkyl or aryl group, or any two groups selected from $R^{11}$, $R^{12}$ and $R^{13}$ may be conjoined to form a ring of 5 to 8 atoms; or (d) —$R^1$ represents, by the structure (II) below, in which the N-atom is incorporated at the bridgehead position in a tricyclic nitrogen heterocycle, and p and q are both integers between 2 and 6 and may be the same or different;

(II)

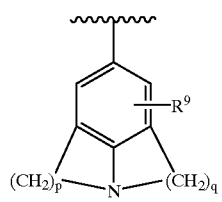

(I)

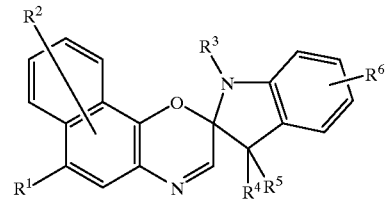

wherein:

(a) —R¹ is selected from the following aminoaryl moieties:

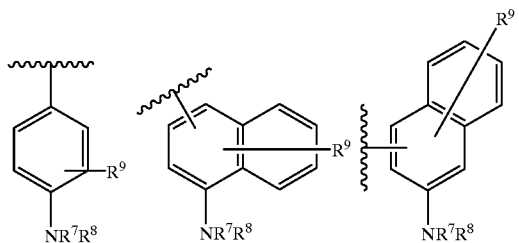

in which $R^7$ and $R^8$, which may be the same or different, are each selected from a linear or branched $C_1$–$C_{20}$ alkyl group, an aryl group, a heteroaryl group, a linear or branched $C_1$–$C_{20}$ alkylaryl group, a linear or branched $C_1$–$C_{20}$ alkyl -cycloalkyl or -bicycloalkyl or -tricycloalkyl or substituted -cycloalkyl or -bicycloalkyl or tricycloalkyl group, a linear or branched $C_1$–$C_{20}$ haloalkyl or perhaloalkyl group, a linear or branched $C_1$–$C_{20}$ alkoxyalkyl or peralkoxyalkyl group, a linear or branched $C_1$–$C_{20}$ alkylthioalkyl or peralkylthioalkyl group, a linear or branched $C_1$–$C_{20}$ aminoalkyl or peraminoalkyl group, a $C_3$–$C_{20}$ cycloalkyl or substituted cycloalkyl group, a $C_4$–$C_{20}$ bicycloalkyl or substituted bicycloalkyl group, a $C_6$–$C_{20}$ tricycloalkyl or substituted tricycloalkyl group, a linear or branched $C_1$–$C_{20}$ hydroxyalkyl or a perhydroxyalkyl group; or (b) —R' is selected from cyclic aminoaryl moieties in which $R^7$ and $R^8$ are conjoined according to the following structures:

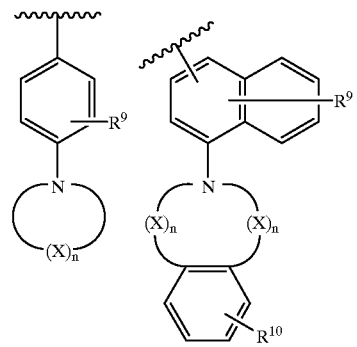

and wherein —R³ is a linear or branched $C_1$–$C_{20}$ alkyl group, a linear or branched $C_2$–$C_{20}$ alkenyl or polyalkenyl group in any E or Z geometrical isomeric form, a $C_2$–$C_{20}$ alkynyl or polyalkynyl group, an aryl group, a heteroaryl group, a linear or branched $C_1$–$C_{20}$ alkyl aryl group, a linear or branched $C_1$–$C_{20}$ alkyl -cycloalkyl or -bicycloalkyl or -tricycloalkyl or substituted -cycloalkyl or -bicycloalkyl or tricycloalkyl group, a linear or branched $C_1$–$C_{20}$ haloalkyl or perhaloalkyl group, a linear or branched $C_1$–$C_{20}$ alkoxyalkyl or peralkoxyalkyl group, a linear or branched $C_1$–$C_{20}$ alkylthioalkyl group, a $C_3$–$C_{20}$ cycloalkyl or substituted cycloalkyl group, a $C_4$–$C_{20}$ bicycloalkyl or substituted bicycloalkyl group, a $C_6$–$C_{20}$ tricycloalkyl or substituted tricycloalkyl group;

or a linear or branched $C_1$–$C_{20}$ hydroxyalkyl or perhydroxyalkyl group; and wherein —R⁴ and —R⁵, which may be the same or different, are each selected from the substituents specified above for —R³ above, or —R⁴ and —R⁵ may be conjoined to form a spiro linked $C_3$–$C_{20}$ cyclic system or substituted system;

and wherein —R⁶ of which there may be none, one or more than one, and which may be the same or different are each selected from H, $C_1$–$C_{20}$, linear or branched alkyl, $C_1$–$C_{20}$ linear or branched alkoxy, $C_1$–$C_{20}$ linear or branched dialkylthio, hydroxy, amine, $C_1$–$C_{20}$ linear or branched alkylamino or branched alkylamino, $C_1$–$C_{20}$ linear or branched dialkylamino, $C_1$–$C_{20}$ linear or branched alkyl arylamino, diarylamino, arylamino, benzylamino, dibenzylamino, $C_1$–$C_{20}$ linear or branched alkanoylamino, aroylamino and cyclic amino and wherein —R², R⁹ and R¹⁰ of which there may be none, one or more than one, and which may be the same or different, are each selected from hydrogen, halogen, nitro, nitroso, amino, acetamido, $C_2$–$C_{10}$ N-alkylamido, alkoxycarbonyl, nitrile, carboxy, hydroxy, aryloxy, $C_1$–$C_{10}$ alkoxy, a heteroatom which is O or N or S or P which in turn can be bonded either singly or multiply to carbon, oxygen, sulfur or nitrogen, $C_1$–$C_5$ alkoxy or alkythio or aryl or aryloxy or multiples thereof, or —R², —R⁶, R⁹ and R¹⁰ may each be selected from those substituents specified for R³.

2. A photochromic compound having the general formula (I):

-continued

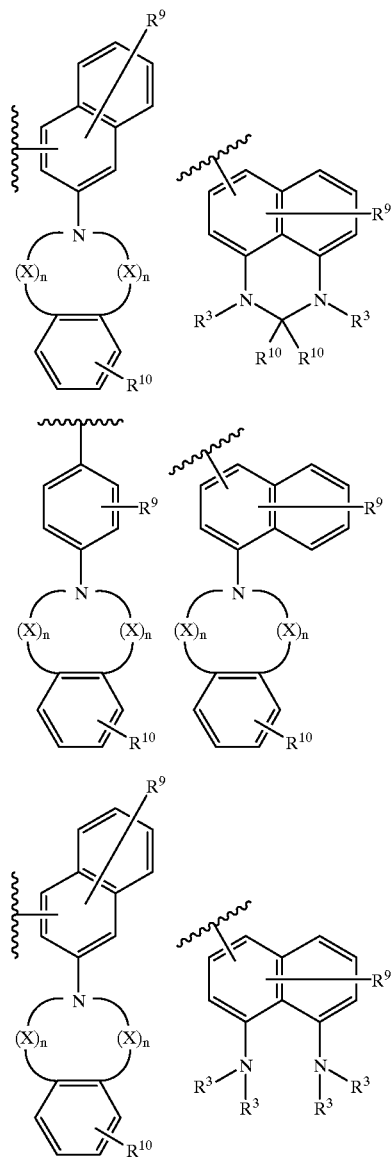

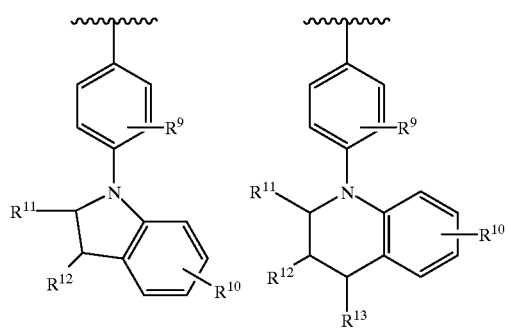

wherein the size of the nitrogen containing ring is from 3 to 40 atoms (inclusive of the N atom) and may incorporate one or more of the same or different groups of atoms (X) which may be arranged in any sequence and where X may be selected from $CH_2$, $CHR^7$, $CRR^7R^8$, CHaryl, $C(aryl)_2$, C(alkyl,aryl),O, S, S(O), $S(O)_2$, NH, N-alkyl, N-aryl, P-alkyl, P-aryl, P(O)alkyl, P(O)aryl, P(O)Oalkyl; wherein $R^7$ and $R^8$ may each be selected from those substituents specified above; or (c) —$R^1$ represents an N-indolinoaryl or N-tetrahydroquinolino aryl substituent of the structure:

wherein $R^{11}$, $R^{12}$ and $R^{13}$ are each a $C_1$–$C_5$, linear or branched alkyl or aryl group, or any two groups selected from $R^{11}$, $R^{12}$ and $R^{13}$ may be conjoined to form a ring of 5 to 8 atoms; or (d) —$R^1$ represents, by the structure (II) below, in which the N-atom is incorporated at the bridgehead position in a tricyclic nitrogen heterocycle, and p and q are both integers between 2 and 6 and may be the same or different;

(II)

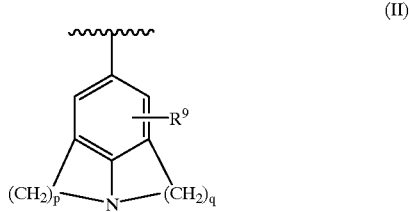

and wherein —$R^3$ is a linear or branched $C_1$–$C_{20}$ alkyl group, a linear or branched $C_2$–$C_{20}$ alkenyl or polyalkenyl group in any E or Z geometrical isomeric form, a $C_2$–$C_{20}$ alkynyl or polyalkynyl group, an aryl group, a heteroaryl group, a linear or branched $C_1$–$C_{20}$ alkyl aryl group, a linear or branched $C_1$–$C_{20}$ alkyl -cycloalkyl or -bicycloalkyl or -tricycloalkyl or substituted -cycloalkyl or -bicycloalkyl or tricycloalkyl group,
a linear or branched $C_1$–$C_{20}$ haloalkyl or perhaloalkyl group, a linear or branched $C_1$–$C_{20}$ alkoxyalkyl or peralkoxyalkyl group, a linear or branched $C_1$–$C_{20}$ alkylthioalkyl group, a $C_3$–$C_{20}$ cycloalkyl or substituted cycloalkyl group,
a $C_4$–$C_{20}$ bicycloalkyl or substituted bicycloalkyl group,
a $C_6$–$C_{20}$ tricycloalkyl or substituted tricycloalkyl group; or a linear or branched $C_1$–$C_{20}$ hydroxyalkyl or perhydroxyalkyl group; and wherein —$R^4$ and —$R^5$, which may be the same or different, are each selected from the substituents specified above for —$R^3$ above, or —$R^4$ and —$R^5$ may be conjoined to form a spiro linked $C_3$–$C_{20}$ cyclic system or substituted system;
and wherein —$R^2$, $R^6$, $R^9$ and $R^{10}$ of which there may be none, one or more than one, and which may be the same or different, are each selected from hydrogen, halogen, nitro, nitroso, amino, acetamido, $C_2$–$C_{10}$ N-alkylamido, alkoxycarbonyl, nitrile, carboxy, hydroxy, aryloxy, $C_1$–$C_{10}$ alkoxy, a heteroatom which is O or N or S or P which in turn can be bonded either singly or multiply to carbon, oxygen, sulfur or nitrogen, $C_1$–$C_5$ alkoxy or alkylthio or aryl or aryloxy or multiples thereof, or —$R^2$, —$R^6$ $R^9$ and $R^{10}$ may each be selected from those substituents specified for $R^3$.

3. A photochromic compound according to claim 2, wherein $R^1$ is 4-diethylaminophenyl,4-dimethylaminophenyl, or 4-pyrrolidinophenyl, $R^3$ is C1–C5 linear or branched alkyl, $R^4$ and $R^5$ are methyl, and $R^6$ is hydrogen, methyl, methoxy, acylamino or halogen.

4. 1,3-Dihydro-1-isobutyl-3,3-dimethyl-6'-(4-N,N-diethyaminophenyl)-spiro-[2H-indole-2,2'[2H]naphth[1,2-b][1,4]oxazine].

5. 1,3-Dihydro-3,3-dimethyl-1-neopentyl-6'-(4-N,N-diethylaminophenyl)-spiro[2H-indole-2,2'[2H]naphth[1,2-b][1,4]oxazine].

6. 5-Acetamido-1,3-dihydro-1,3,3-trimethyl-6'-(4-N,N-diethylaminophenyl)-spiro[2H-indole-2,2'[2H]naphth[1,2-b][1,4]oxazine].

7. 1,3-Dihydro-1-isobutyl-3,3,4,7-tetramethyl-6'-(4-N,N-diethylaminophenyl)-spiro[2H-indole-2,2'[2H]naphth[1,2-b][1,4]oxazine].

8. 1,3-Dihydro-1,3,3-trimethyl-6'-(4-N,N-diethylaminophenyl)-spiro[2H-indole,2,2'[2H]naphth[1,2-b][1,4]oxazine].

9. A process for making a photochromic compound as defined in claim 2, which process includes the following step:

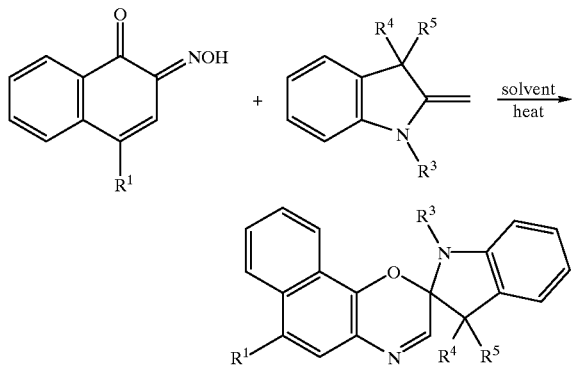

wherein $R^1$, $R^3$, $R^4$ and $R^5$ are defined as in claim 2, or represent groups which can be replaced by, or modified to form, groups as defined respectively in claim 2, and wherein in the above step the reactants and/or product may also include substituents $R^2$ and $R^6$ as defined in claim 2, or such substituents are introduced subsequently.

10. The process according to claim 9, wherein a solution of 4-(4-N,N-dimethylaminophenyl)-1,2-napthoquinone-2-oxime and 1-isobutyl-3,3-dimethyl-2-methyleneindoline and anhydrous ethanol is refluxed until none of such oxime remains.

11. The method according to claim 9, wherein a solution of 4-(4-N,N-dimethylaminophenyl)-1,2-napthoquinone-2-oxime and 3,3-dimethyl-1-neopentyl-2-methyleneindoline in anhydrous ethanol is refluxed until examination of the reaction mixture indicates that no oxime remains.

12. The method of claim 9, wherein a solution of 4-(4-pyrrolidinophenyl)-1,2-naphthoquinone-2-oxime and 1-isobutyl-3,3-dimethyl-2-methyleneindoline in anhydrous ethanol is refluxed until examination of the reaction mixture shows that no oxime remains.

13. The method according to claim 9, wherein 4-(4-N,N-dimethylaminophenyl)-1,2-napthoquinone-2oxime and 1-isobutyl-3,3,4,7-tetramethyl-2-methyleneindoline are reacted to form 1,3-Dihydro-1-isobutyl-3,3,4,7-tetramethyl-6'-(4-N,N-diethylaminophenyl)-spiro[2H-indole-2,2'[2H] naphth[1,2-b][1,4]oxazine].

14. The method according to claim 9, wherein 4-(4-pyrrolidinophenyl)-1,2-naphthoquinone-2-oxime and 1,3,3-trimethyl-2-methylene-5-nitroindoline are reacted to form 1,3-Dihydro-1,3,3-trimethyl-5-nitro-6'-(4-pyrrolidinophenyl)spiro-[2H-indole-2,2'[2H]naphth[1,2-b][1,4]oxazine].

15. The method of claim 9, wherein 4-(4-N,N-diethylaminophenyl)-1,2-napthoquinone-2-oxime and 5-methoxy-1,3,3-trimethyl-2-methyleneindoline are reacted to form 1,3-Dihydro-5-methoxy-1,3,3-trimethyl-6'-(4-N,N-diethylaminophenyl)-spiro[2H-indole-2,2'[2H]naphth[1,2-b][1,4]oxazine].

16. The method according to claim 9, wherein 4-(4-N,N-diethylaminophenyl)-1,2-napthoquinone-2-oxime and 5-acetamido-1,3,3-trimethyl-2-methyleneindoline are reacted to form 5-Acetamideo-1,3-dihydro-1,3,3-trimethyl-6'-(4-N,N-diethylaminophenyl)-spiro[2H-indole-2,2'[2H] naphth[1,2-b][1,4]oxazine].

17. The method according to claim 9, wherein 4-(4-N,N-diethylaminophenyl)-1,2-napthoquinone-2-oxime and 5-cyano-1,3,3-trimethyl-2-methyleneindoline are reacted to form 5-Cyano-1,3-dihydro-1,3,3-trimethyl-6'-(4-N,N-diethylaminophenyl)-spiro[2H-indole-2,2'[2H]naphth[1,2-b][1,4]oxazine].

18. The method according to claim 9, wherein 4-(4-N,N-diethylaminophenyl)-1,2-napthoquinone-2-oxime and 3,3-dimethyl-1-isobutyl-2-methylene-5-trifluoromethylindoline are reacted to form 1,3-Dihydro-1-isobutyl-3,3-dimethyl-5-trifluoromethyl-6'-(4-N,N-diethylaminophenyl)-spiro[2H-indole-2,2'[2H]naphth[1,2-b][1,4]oxazine].

19. The method according to claim 9, wherein 4-(4-N,N-diethylaminophenyl)-1,2-napthoquinone-2oxime and 5,7-dimethoxy-3,3-dimethyl-1-isobutyl-2-methyleneindoline are reacted to form 1,3-Dihydro-1-isobutyl-5,7-dimethoxy-3,3-dimethyl-6'-(4-N,N-diethylaminophenyl)-spiro[2H-indole-2,2'[2H]naphth[1,2-b][1,4]oxazine].

20. The method according to claim 9, wherein 4-(4-N,N-diethylaminophenyl)-1,2-napthoquinone-2oxime and 3,3-dimethyl-1-neopentyl-2-methyleneindoline are reacted to form 1,3-Dihydro-3,3-dimethyl-1-neopentyl-6'-(4-N,N-diethylaminophenyl)-spiro[2H-indole-2,2'[2H]naphth[1,2-b][1,4]oxazine].

21. A photochromic composition which comprises a photochromic compound according to claim 2.

22. An article which includes a photochromic compound according to claim 2.

23. An optical element which includes a photochromic compound according to claim 2.

* * * * *